(12) United States Patent  (10) Patent No.: US 8,277,410 B2
Watson  (45) Date of Patent: Oct. 2, 2012

(54) METHODS AND APPARATUS FOR INHIBITING INTRODUCTION OF AIR INTO THE VASCULATURE DURING A PERCUTANEOUS PROCEDURE

(75) Inventor: James R. Watson, Santa Rosa, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/403,291

(22) Filed: Mar. 12, 2009

(65) Prior Publication Data

US 2009/0234320 A1 Sep. 17, 2009

Related U.S. Application Data

(60) Provisional application No. 61/036,437, filed on Mar. 13, 2008.

(51) Int. Cl.
*A61M 1/00* (2006.01)
(52) U.S. Cl. .................................. 604/122; 604/124
(58) Field of Classification Search .................. 604/122, 604/124–126
See application file for complete search history.

(56) References Cited

U.S. PATENT DOCUMENTS

| 5,419,774 | A | 5/1995 | Willard et al. |
| 5,542,931 | A | 8/1996 | Gravener et al. |
| 5,895,376 | A | 4/1999 | Schwartz |
| 6,126,092 | A * | 10/2000 | Cote et al. ................ 239/422 |
| 2004/0220519 | A1 | 11/2004 | Wulfman et al. |
| 2005/0027253 | A1* | 2/2005 | Castellano et al. ........ 604/122 |
| 2007/0287158 | A1* | 12/2007 | Gorodeski et al. ........... 435/6 |
| 2008/0009794 | A1 | 1/2008 | Bagaoisan et al. |
| 2008/0234631 | A1 | 9/2008 | Reis |

FOREIGN PATENT DOCUMENTS

| WO | WO 2007/089309 A2 | 8/2007 |
| WO | WO 2008/115565 A2 | 9/2008 |

OTHER PUBLICATIONS

PCT International Search Report and Written Opinion dated May 11, 2009 for PCT app. Ser. No. PCT/US2009/003026.

* cited by examiner

*Primary Examiner* — Kevin C Sirmons
*Assistant Examiner* — Brandy C Scott
(74) *Attorney, Agent, or Firm* — Henricks, Slavin & Holmes LLP

(57) ABSTRACT

Apparatus and methods for inhibiting the introduction of air into the body during a percutaneous procedure. The apparatus may include an instrument passage lumen defining a degassing region with a degassing region distal end and a degassing region proximal end, a fluid inlet port at the degassing region distal end, and a fluid outlet port at the degassing region proximal end. So configured, fluid will flow only from the degassing region distal end to the degassing region proximal end.

20 Claims, 7 Drawing Sheets

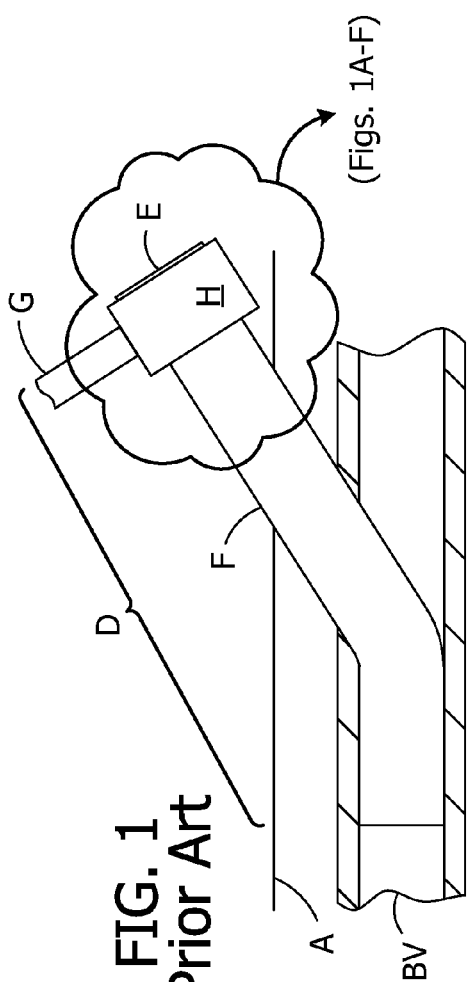
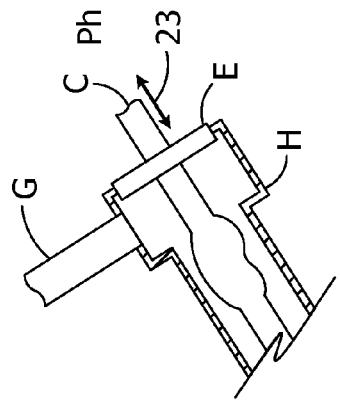
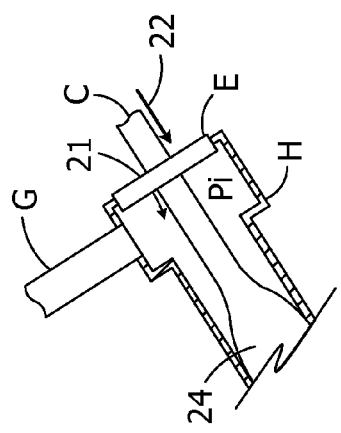
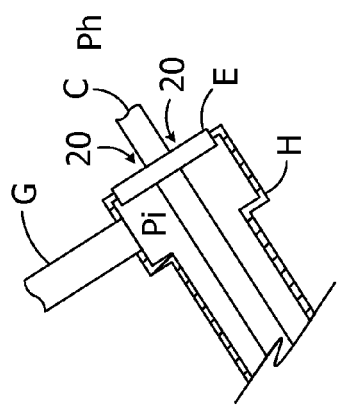

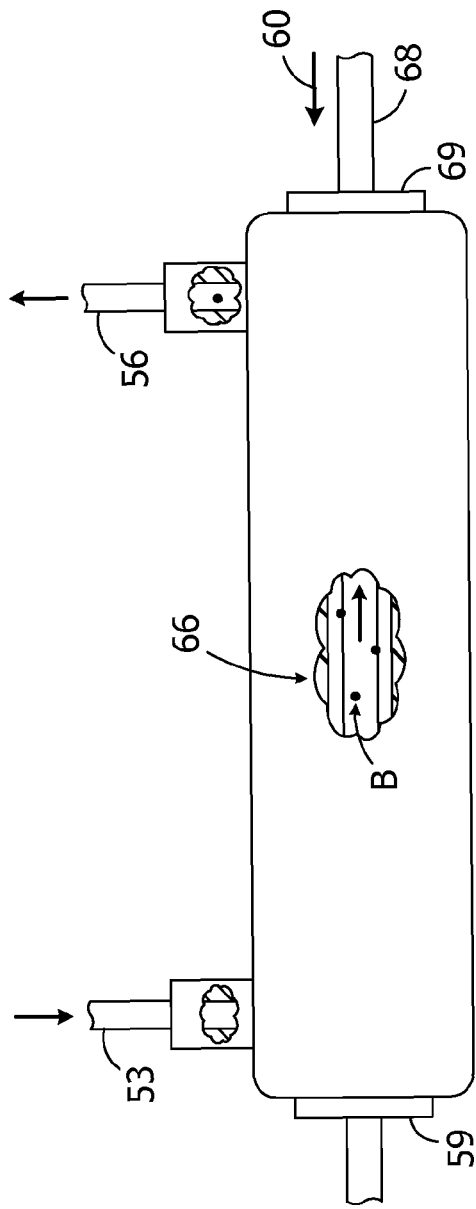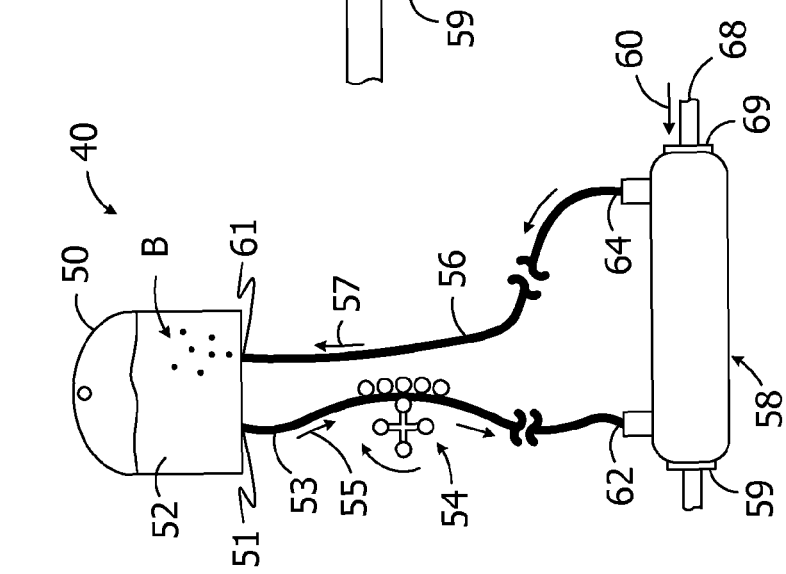
FIG. 2A
FIG. 2

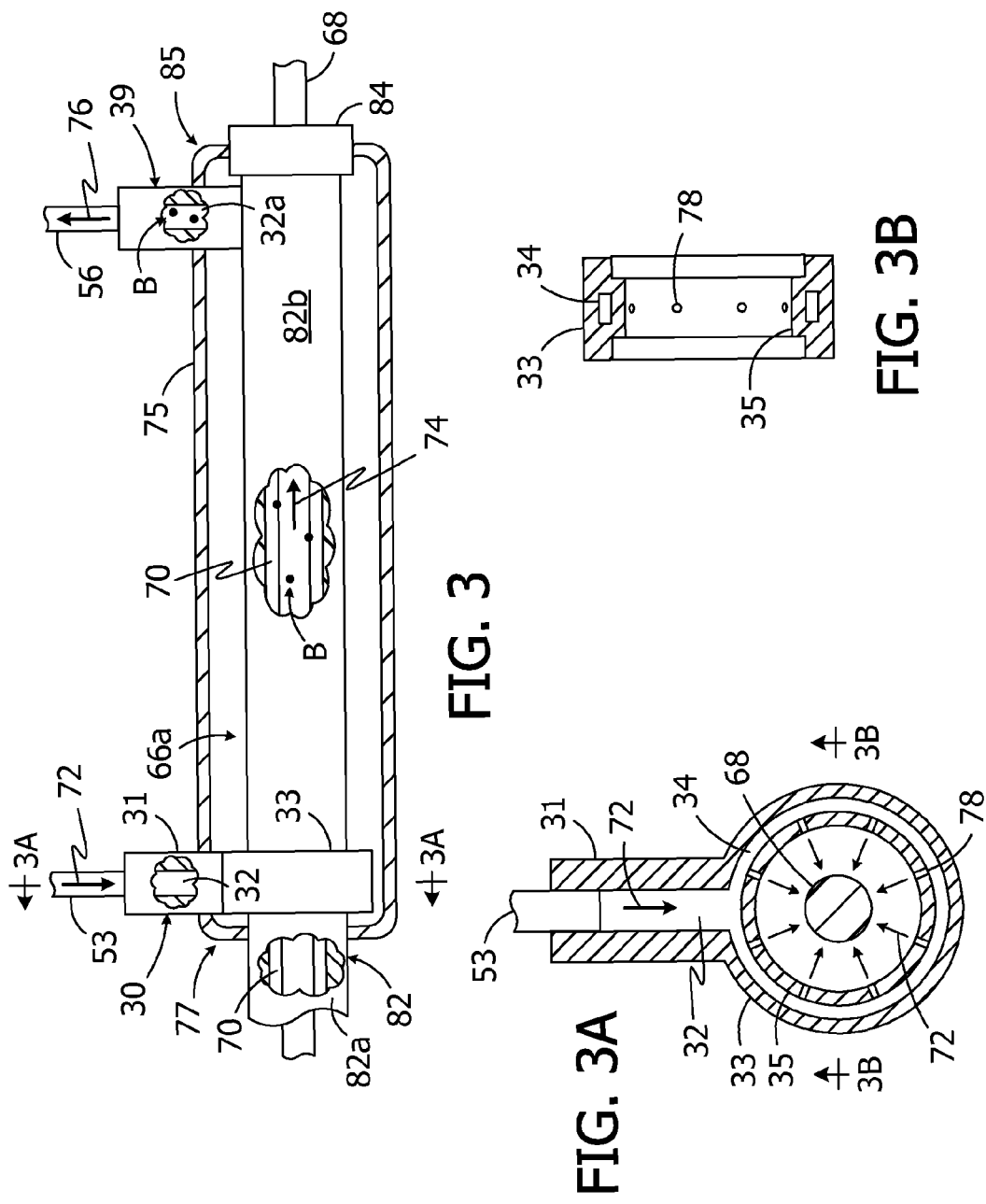

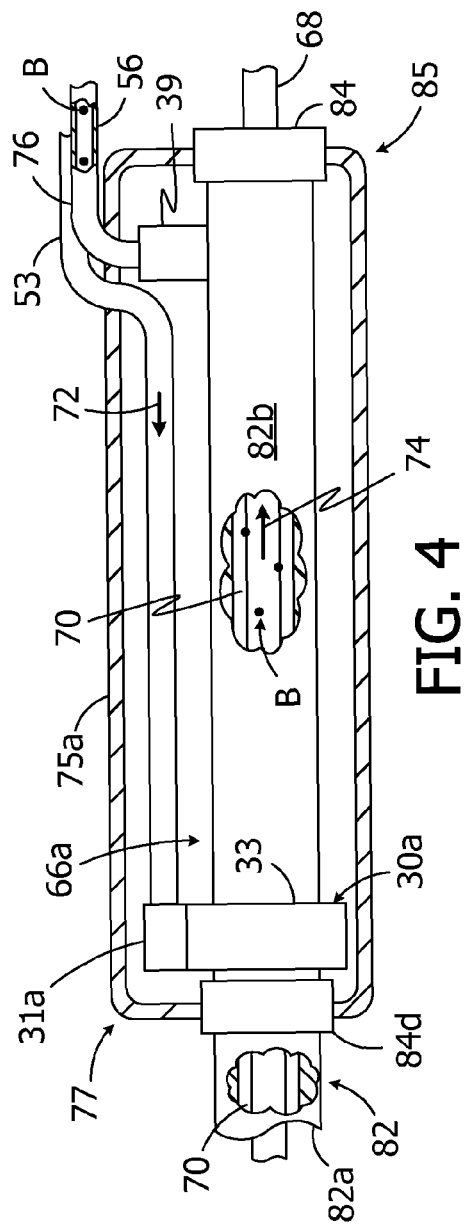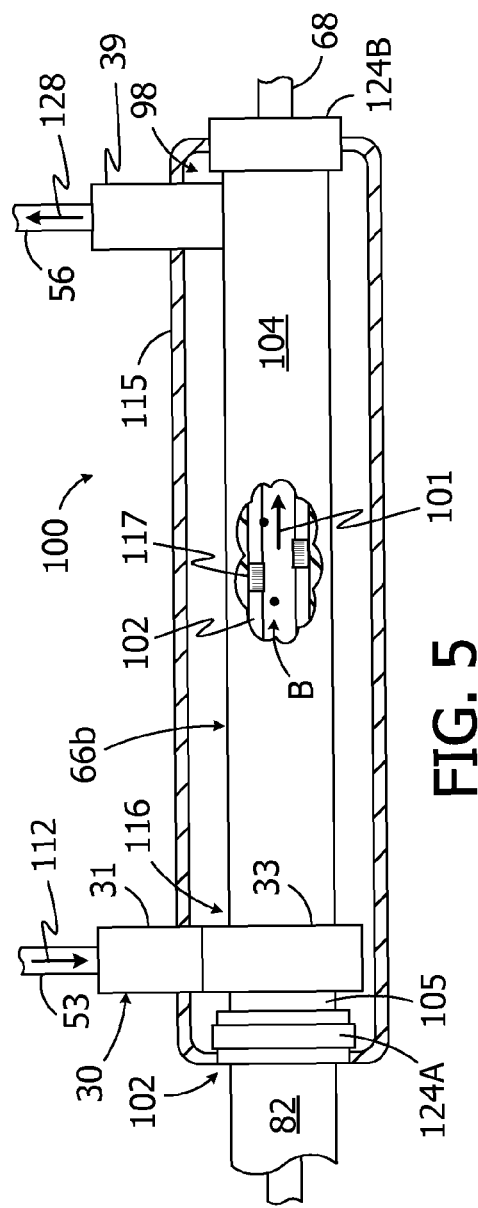

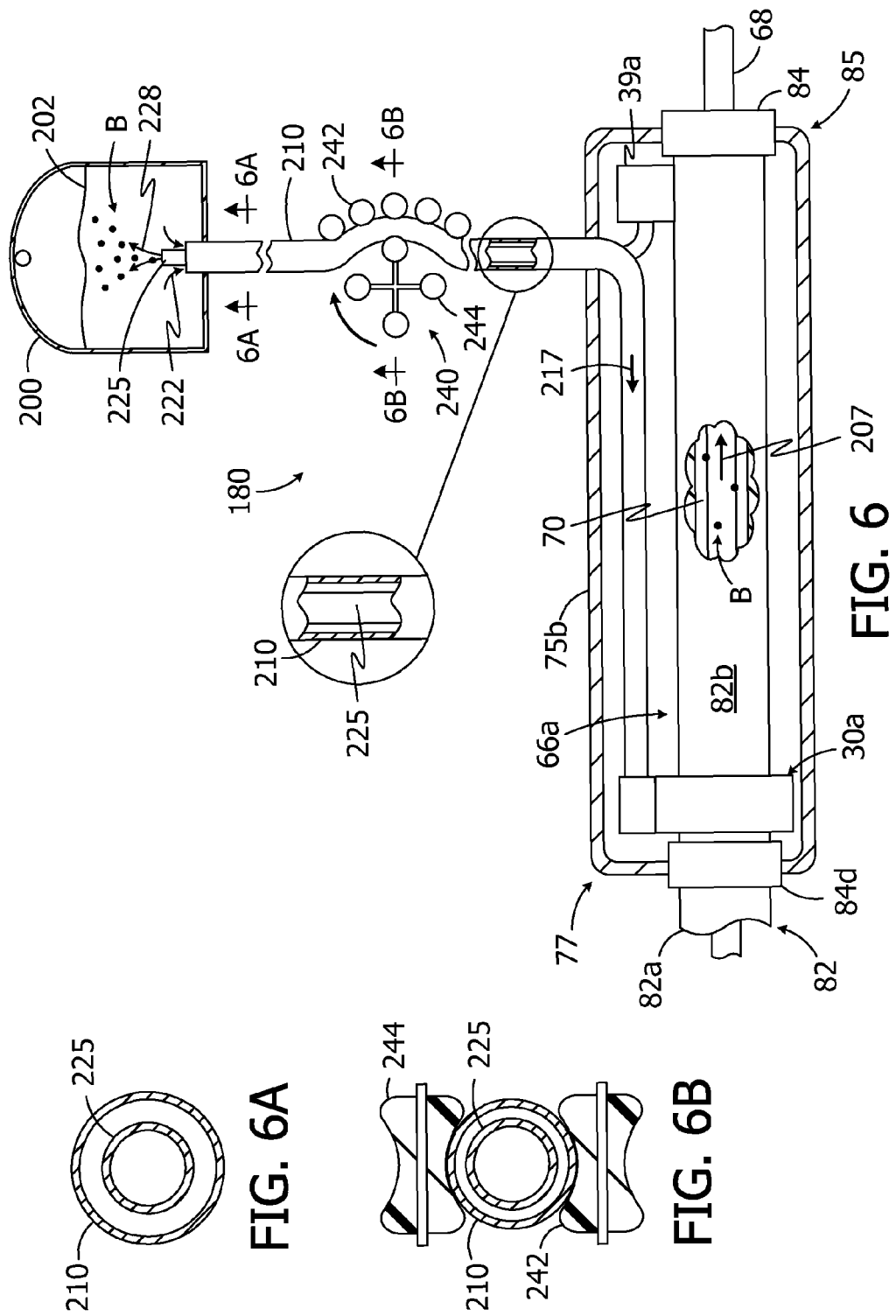

METHODS AND APPARATUS FOR INHIBITING INTRODUCTION OF AIR INTO THE VASCULATURE DURING A PERCUTANEOUS PROCEDURE

CROSS-REFERENCE TO RELATED APPLICATION

This application claims the benefit of U.S. Provisional Application Ser. No. 61/036,437 filed Mar. 13, 2008 and entitled "Methods And Apparatus For Inhibiting Introduction Of Air Into The Vasculature During A Percutaneous Procedure," which is incorporated herein by reference in its entirety.

FIELD OF THE INVENTIONS

The disclosed inventions pertain to methods and apparatus for inhibiting the introduction of air into the vasculature of a patient during percutaneous procedures such as, for example, percutaneous diagnostic, therapeutic and interventional procedures.

BACKGROUND

For many diagnostic, therapeutic, or interventional percutaneous procedures involving the human vasculature, maintaining hemostasis is critical not only to prevent loss of blood, but also to prevent the introduction of air into the patient's vasculature system. Devices such as angioplasty balloon catheters, coronary guidewires, radio frequency (RF) ablation catheters, cryo-therapy catheters, and neurovascular occlusive device delivery catheters are just a sample of what is commonly used percutaneously to treat a wide variety of illnesses. The introduction of air into the blood stream can be quite serious, resulting in a stroke if it is allowed to migrate to the heart or brain (depriving the tissue of oxygenated blood).

FIG. 1 depicts the main components of an exemplary vasculature access device D, including a proximal hub H and a distal shaft F shown extending through an incision made in the patient's skin surface A and a puncture tract extending through the subcutaneous tissue and into a blood vessel BV of the patient's vasculature. With reference also to FIGS. 1A-1F, the proximal hub H includes a hemostasis port E that allows for access of a diagnostic, therapeutic or interventional instrument C to pass through the hub H and distal shaft F, respectively, into the blood vessel BV. A fluid-flush port G is also provided on the hub, as is well-known.

The present inventor has determined that introduction of air through the hemostasis valve E into the hub H for possible downstream migration to the vasculature may happen for a number of reasons. With reference to FIG. 1A, air can pass from the external environment through the hemostasis valve E, as indicated by arrows 20, while the instrument C is being passed through the hemostasis valve E, due to the valve design and a pressure differential i.e., when the pressure Pi within the interior of the hub H is less than the ambient pressure Ph. With reference to FIG. 1B, air can pass from the external environment through the hemostasis valve E, as indicated by arrow 21, when a pressure differential is created due to the movement of the instrument C, indicated by arrow 22, resulting from the instrument C acting as an "occlusive plug" 24 that creates a lower pressure Pi on the proximal side of the instrument within the hub H. With reference to FIG. 1C, air can pass from the external environment through the hemostasis valve E when the valve E is deformed or damaged by the passage of the instrument C, indicated by arrow 23, such as during multiple expansion/contraction cycles caused by interchanging a catheter and dilator. Air can also pass from the external environment through the hemostasis valve E while the instrument C is in place, due vigorous aspiration via the flush-port G, as indicated by arrows 20, 25 and 26, shown amongst the incoming air bubbles B in FIG. 1D. With reference to FIG. 1E, air can also pass from the external environment through the hemostasis valve E due to normal aspiration through the flush-port G, as indicated by arrows 27, when the valve E fails to recover to create a seal after the instrument C has been removed. With reference to FIG. 1F, it is also worth noting that air bubbles B drawn into the interior of the hub H, as indicated by arrows 28, may cling to the instrument C due to surface tension, indicated by reference number 29, and be drawn into the vasculature along with the instrument C.

The present inventor has also determined that it would be desirable to avoid this introduction of air into the interior hub H of the access device D, since this air can migrate through the distal shaft F and into the patient's vasculature.

SUMMARY

The present methods and apparatus inhibit the above-described introduction of air into the vasculature during percutaneous procedures by, in at least some embodiments, creating a sterile fluid flow (mixing with the patient's blood) in a proximal portion of the access device or of an adjunct device coupled to the proximal end of the vascular access device, through which the various instruments are passed. The present methods and apparatus are suitable for a wide range of percutaneous applications, including ones not involving the vasculature, whenever inhibiting the introduction of air into the body is desired.

In one embodiment, a "degassing section" is located in a proximal end portion of the vascular access device, for example just distally of the hemostasis valve through which the various instruments may be introduced. The degassing section may be part of a system for inhibiting the introduction of air into the body during a percutaneous procedure that also includes a container supplied with sterile fluid (e.g., a plastic bag of hepanized saline). The system may also include a supply line, which has a first end in fluid communication with the sterile fluid container and a second end in fluid communication with the degassing section, and a return line, which has a first end in fluid communication with the degassing section and a second end in fluid communication with the sterile fluid container. A closed-loop fluid circulation system may be formed by the degassing section of the access device, the container, and the supply and return lines. A pump, such as a peristaltic pump, may be provided along the supply line to cause circulation of the sterilized fluid through the degassing section, for example in a distal-to-proximal direction, i.e., with the supply line in fluid communication with a more distal portion of the degassing section than the return line. In particular, air bubbles that may be introduced into the access device through the proximal end hemostasis valve are collected by the circulating flow of sterile fluid in the degassing section and pushed through the return line into the sterile fluid container.

In one embodiment, the degassing section is incorporated into a proximal handle of a vascular access sheath. The sheath may be of a type introduced "bareback" into the vasculature (as is well-known), and has an interior working lumen passing through the handle through which various elongate instruments (e.g., stylet/dilator sets, guidewires and catheters) are introduced into the vasculature through a hemostasis valve located in a proximal end of the handle. The respective supply and return lines are coupled to the handle, with the supply line placed in fluid communication with the interior working lumen of the sheath in a distal portion of the handle, and the return line placed in fluid communication with the interior working lumen in a proximal portion of the handle, the section of the working lumen between the respective supply and return lines defines the degassing section.

In another embodiment, the degassing section is incorporated into an adjunct device that is coupled to a distal end of a standard vascular access device (or sheath). The adjunction device has a distal end opening that is coupled in a fluidly-sealed manner to the proximal hemostasis valve of the vascular access device (or sheath). The adjunct device comprises its own proximal end hemostasis valve through which the various elongate instruments are introduced, passing through the adjunct device degassing section, which may be defined by a lumen within the device, then through the access device hemostasis valve and into the vasculature. The respective supply and return lines may be coupled to the adjunct device with the supply line in fluid communication with a distal end portion of the interior degassing section and the return line in fluid communication with a proximal end portion of the interior degassing section.

In variations of the above embodiments, the respective supply and return lines may be provided in a co-axial arrangement to reduce the number of individual fluid flow lines coupled to the vascular access device. Alternatively, the fluid supply line may be gravity fed into the degassing section of the vascular access device or adjunct device (with no pump needed), and instead of a return line to the sterile fluid container, the fluid outflow from the degassing section may be gravity expelled to a drain line.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings. The systems and apparatus shown in the drawings are not necessarily drawn to scale, with emphasis instead being placed on illustrating the various aspects and features of the depicted embodiments.

FIG. 1 is a partially cut-away side view showing a conventional vascular access device inserted percutaneously into a patient's blood vessel.

FIGS. 1A-1F are partially cut-away side views of the proximal hub portion of the vascular access device shown in FIG. 1, illustrating various scenarios in which air can enter into the access device and patient's vasculature through a proximally located hemostasis valve.

FIG. 2 is a schematic illustration of a system in accordance with one embodiment of a present invention.

FIG. 2A is a side, partially cut-away view of a portion of the system illustrated in FIG. 2.

FIG. 3 is a side, partially cut-away view of an apparatus in accordance with one embodiment of a present invention.

FIG. 3A is a section view take along line 3A-3A in FIG. 3.
FIG. 3B is a section view take along line 3B-3B in FIG. 3A.
FIG. 4 is a side, partially cut-away view of an apparatus in accordance with one embodiment of a present invention.
FIG. 5 is a side, partially cut-away view of an apparatus in accordance with one embodiment of a present invention.

FIG. 6 is a schematic illustration of a system in accordance with one embodiment of a present invention.
FIG. 6A is a section view take along line 6A-6A in FIG. 6.
FIG. 6B is a section view take along line 6B-6B in FIG. 6.

DETAILED DESCRIPTION OF THE EXEMPLARY EMBODIMENTS

Figure 1F:
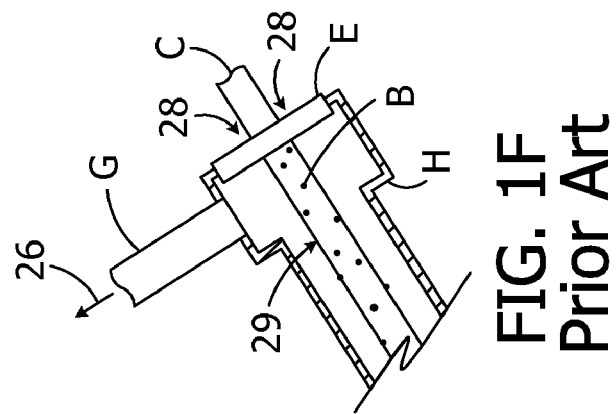
Figure 1E:
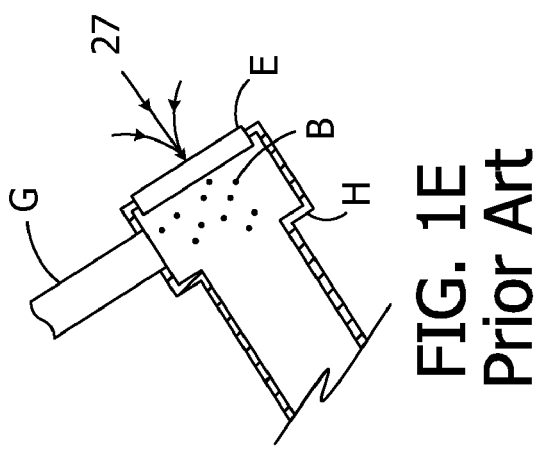
Figure 1D:
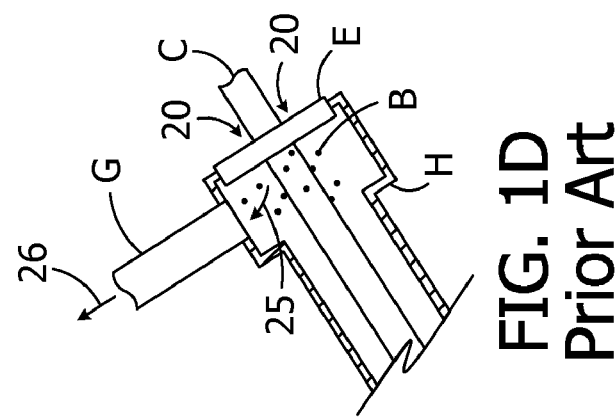

The following is a detailed description of the best presently known modes of carrying out the inventions. This description is not to be taken in a limiting sense, but is made merely for the purpose of illustrating the general principles of the inventions.

FIGS. 2 and 2A depict a system 40 for inhibiting the introduction of air into a vascular access device and a patient's vasculature according to one embodiment of at least one of the present inventions. The system 40 generally includes a container 50, e.g., a standard plastic "iv" bag, filled or partially filled with sterile fluid 52, e.g., hepanized saline. A supply line 53 has a first end 51 in fluid communication with the sterile fluid container 50 and a second end 62 in fluid communication with a degassing section 66 located in a device 58 (e.g. by way of a port). The device 58 may, for example, be the proximal end portion of a vascular access device or may be an adjunct device that is coupled to a proximal end of a vascular access device. The exemplary device 58 includes distal and proximal end hemostasis valves 59 and 69, through which various elongate working instruments may be introduced. The degassing section 66 in the illustrated implementation extends from a point just proximal of the distal end hemostasis valve 59 to a point just distal of the proximal end hemostasis valve 69. For purposes of illustration, an exemplary instrument 68 is shown placed through the proximal hemostasis valve 69, extending through the degassing section 66, through the distal hemostasis valve 59, and heading towards the vasculature, as indicated by arrow 60, in FIGS. 2 and 2A.

A return line 56 has a first end 64 in fluid communication with the degassing section 66 of the device 58 (e.g. by way of a port) and a second end 61 in fluid communication with the sterile fluid container 50. A closed-loop fluid circulation system is defined by the fluid container 50, the supply and return lines 53 and 56, and the degassing section 66. A peristaltic pump 54, or other suitable pump, is provided along the supply line 56 to cause circulation of sterilized fluid 52 through the degassing section 66 in a distal-to-proximal direction that is the same direction as blood flow from the patient (i.e. is antegrade), as indicated by arrows 55 and 57. In particular, air bubbles B that may be introduced into the access device through the proximal end hemostasis valve 69 are collected by the circulating flow of sterile fluid 52 in the degassing section 66 and pushed through the return line 53 into the sterile fluid container 50. The locations of the junctions 51 and 61 of the respective supply and return lines 53 and 56 may be spaced apart on the container 50, as shown, to prevent the air bubbles B pushed into the container 50 through the return line 56 from re-entering the degassing section 66 through the supply line 53.

The return line 56 and container 50 may be formed from a clear plastic material to allow for visual confirmation that air bubbles B are being removed from the degassing section 66 and pushed through the return line 56 into the container 50. It should also be appreciated that many variations of the exemplary embodiment illustrated in FIGS. 2 and 2A are possible. By way of non-limiting example, the respective supply and return lines 53 and 56 may be provided in a co-axial arrangement to reduce the number of individual fluid flow lines coupled to the vascular access device (one such embodiment is described below in conjunction with FIG. 6). Also, the fluid supply line 53 may be gravity fed into the degassing section of the vascular access device or adjunct device (i.e., with no pump 54 needed), wherein instead of the return line to the sterile fluid container 50, the fluid outflow from the degassing section may be gravity expelled to a drain line.

Referring to FIGS. 3-3B, a degassing section 66a may be incorporated into the proximal handle 75 of a device that also includes a vascular access sheath 82. The handle 75, which may be in the form of a housing that defines distal and proximal ends 77 and 85, may be connected to the container 50 and to the supply and return lines 53 and 56 to form a system in the manner described above with reference to FIGS. 2 and 2A. The sheath 82 may be of a type introduced "bareback" into the vasculature (as is well-known), and has an interior working lumen 70, through which various elongate instruments (e.g., stylet/dilator sets, guidewires, and catheters; collectively represented by reference numeral 68 in FIGS. 3 and 3A) may be introduced into the vasculature through a hemostasis valve 84 located at the proximal end 85 of the handle 75. The supply and return lines 53 and 56 are physically secured (either permanently or temporarily) to the handle 75, and are fluidically connected to the degassing section 66a, by connectors (or ports) 30 and 39.

The exemplary connector 30 includes a tubular portion 31 with a lumen 32, which may be connected to the supply line 53, and an annular portion 33, which delivers fluid to the sheath lumen 70. Referring more specifically to FIGS. 3A and 3B, the annular portion 33 delivers fluid, as indicated by arrows 72, to various points around the perimeter the instrument 68. Delivering fluid around the perimeter of the instrument 68 as it exits the supply line 53, as opposed to merely delivering fluid to the side of the instrument that faces tubular portion 31, insures that all air bubbles near the distal end of the degassing section 66a will be driven proximally away from the vasculature. There are a variety of ways to connect the annular portion 33 of the connector 31 to the lumen 70 within the access sheath 82. In the illustrated embodiment, the annular portion 33 includes an annular lumen 34 that is connected to the tubular portion lumen 31, an abutment 35, and a plurality of openings 78 that are connected to the annular lumen. The sheath 82 is a two-part structure that includes first and second sheath portions 82a and 82b which abut opposite sides of the abutment 35 and are connected to the annular portion 33 by adhesive or some other suitable instrumentality. In another exemplary implementation, the abutment may be omitted and the sheath may be a unitary structure with fluid openings that are aligned with the connector openings 78. The connector 39 includes a lumen 32a that is in fluid communication with the sheath lumen 70. The portion of the sheath lumen 70 between the connectors 30 and 39 defines the degassing section 66a.

It should be noted that the connectors 30 and 39 are located at the distal and proximal ends 77 and 85 of the handle 75 and define the distal and proximal ends of the degassing section 66a. As such, all fluid flow though the degassing section 66a is distal-to-proximal, i.e. away from the vasculature. As such, air bubbles B that may be introduced into the sheath lumen 70 through the proximal end hemostasis valve 84 are collected by the circulating flow of sterile fluid in the degassing section 66a, as indicated by flow arrows 72, 74 and 76, and are pushed into the return line 56. A variety of modifications may be made to this embodiment. By way of non-limiting example, the fluid connection between the supply line 53 and the sheath lumen 70 may be accomplished by means other than the openings 78, for example, by using a convention "Y" connector or other type of inlet port. It should also be noted that the exemplary embodiment illustrated in FIGS. 3-3B does not include a distal end hemostasis valve and that fluid is delivered to the sheath lumen 70 at a pressure equal to blood pressure in order to insure that the fluid does not travel distally from the connector 30. In other implementations that are otherwise identical to that illustrated in FIGS. 3-3B, a hemostasis valve may be provided distal of the connector 30.

The exemplary handle 75a illustrated in FIG. 4 is substantially similar to the handle 75 illustrated in FIGS. 3-3B and may be employed in the system illustrated in FIG. 2. Here, however, the supply and return lines 53 and 56 used for circulating the sterile fluid that removes air bubbles B from the portion of the sheath lumen 70 that defines the degassing section 66a may be tethered or otherwise connected (e.g., using a "figure 8" style tubing set) and physically coupled near one longitudinal end of the sheath handle 75a in order to reduce the possibility of entanglement during a procedure. The tubular portion 31a of the connector 30a includes a lumen (not shown) that bends at a 90 degree angle to accommodate the redirection of the supply line to the proximal end 85. The exemplary handle 75a also includes a distal end hemostasis valve 84d may be interposed across the sheath lumen 70 at the distal end 77 of the handle 75a to further isolate the degassing section 66a.

One example of an adjunct device that may be coupled to the distal end of standard vascular access device, and employed in the system illustrated in FIG. 2, is generally represented by reference numeral 100 in FIG. 5. The exemplary adjunct device 100 includes a degassing section 66b within a housing 115 that is coupled, e.g., by a clip-on or clamshell manner, to the proximal hemostasis valve 124A of a standard vascular access device (or sheath) 82. The degassing section 66b is defined by the internal lumen 102 of a tube 104. The distal end of the lumen 102 is connected to the supply line 53 by the above-described connector 30 with fluid openings 78 (FIGS. 3A and 3B), while the proximal end of the lumen 102 is connected to the return line 56 by the above-described connector 39. As such, fluid is received at the distal end 116 of the degassing section 66b and is removed at the proximal end 98 of the degassing section. The access device hemostasis valve 124A may be directly connected to the connector annular portion 33, connected to the connector annular portion 33 by a short tube 105 (as shown), or connected to the tube 104 in those instances where the tube 104 is provided with holes that are aligned with the connector fluid openings 78 (FIGS. 3A and 3B). The adjunct device 100 also includes a proximal end hemostasis valve 124B, through which the various elongate instruments are introduced, passing through the degassing section 66b, and then through the access device hemostasis valve 124A and into the vasculature. As with the above-described embodiments, air bubbles B that may be introduced into the lumen 102 (and degassing section 66b) through the proximal end hemostasis valve 124B are collected by the circulating flow of sterile fluid in the degassing section 66b and pushed into the return line 56, as indicated by arrows 112, 101 and 128.

The exemplary adjunct device 100 illustrated in FIG. 5 also includes one or more brushes 117 positioned within the degassing section 66b, for example on the interior wall of tube 104, to facilitate moving of air bubbles B away from the wall and/or instrument 68 and into the fluid flow stream without substantially impeding fluid flow. The exemplary implementation includes a plurality of brushes 117 which are longitudinally and circumferentially offset from one another along a length of the degassing section 66b to minimize any resulting flow impedance. The brushes 117 may also be employed in any of the other implementations described herein.

Another exemplary system for inhibiting the introduction of air into a vascular access device and a patient's vasculature is generally represented by reference numeral 180 in FIG. 6. Similar to system 40 (FIG. 2), fluid is used to remove air and, to that end, the system 180 generally includes a sterile fluid container 200, e.g., a standard plastic "iv" bag, filled or partially filled with sterile fluid 202, e.g., hepanized saline. The exemplary system also includes a handle 75b that is a portion of a device that also includes a vascular access sheath 82, although other embodiments may include an adjunct device coupled to a proximal end of a vascular access device. The handle 75b is substantially similar to the handle 75 illustrated in FIGS. 3-3B and similar elements are represented by similar reference numerals. The system 180 also includes a supply line 210 with a first end in fluid communication with the sterile fluid container 200 (and fluid 202) and a second end connected to and in fluid communication with the distal end of the degassing section 66a by a connector 30a in the manner described above. The system 180 also includes a return line 225 with a first end connected to and in fluid communication with the proximal end of the degassing section 66a by way of a connector 39a and a second end in fluid communication with the sterile fluid container 200 (and fluid 202). As such, a closed-loop fluid circulation system that includes the degassing section 66a is provided.

In contrast to the exemplary system 40 illustrated in FIG. 2, the supply and return lines 210 and 225 in system 180 are in a coaxial arrangement (note FIGS. 6 and 6A). The return line 225 extends out of the open end of the supply line 210 within the interior of the fluid container 200. Arrows 228 in FIG. 6 show the fluid outflow with air bubbles B from return line 225, and arrows 222 show the fluid intake into the supply line 210. Within the handle 75b, the supply line 210 separates from the return line 225 and feeds the degassing passage 66a through the plurality of openings 78 (FIGS. 3A and 3B) in the connector 30a. As with the previously described embodiments, the fluid connection between the supply line 210 and the degassing passage 66a may be accomplished by instrumentalities other than the openings 78 of the connector 30a. For example, a "Y" connector or some other conventional inlet port may be used.

Figure 6D:
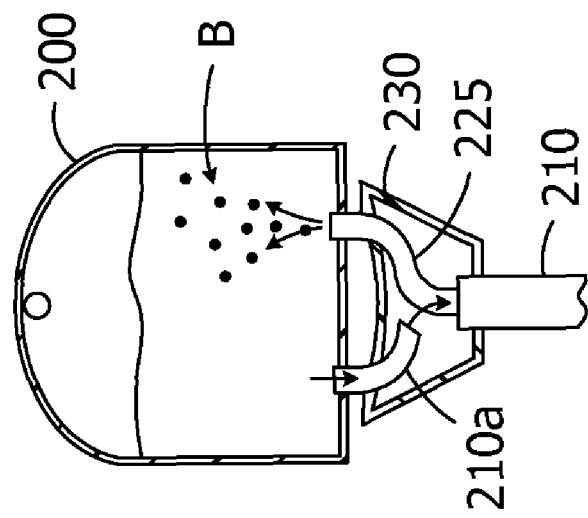
FIG. 6D is front, partially cut-away view of a portion of a system in accordance with one embodiment of a present invention.
Figure 6C:
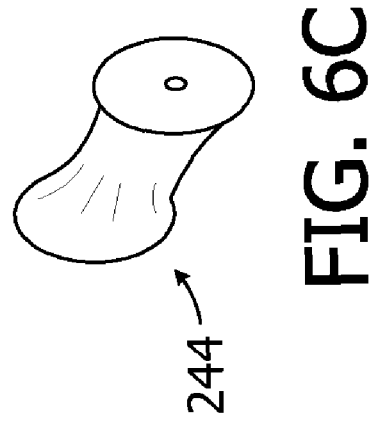
FIG. 6C is a perspective view of a portion of the system illustrated in FIG. 6.

A specialized peristaltic pump 240 is provided along the coaxial supply/return line 210/225, to cause circulation of the sterilized fluid 202 through the degassing section 66a a distal-to-proximal direction, as indicated by the flow arrows 207 and 217. Air bubbles B that may be introduced into the access device through the proximal end hemostasis valve 84 are collected by the circulating flow of sterile fluid 202 in the degassing section 66a (arrow 207) and pushed through the return line 225 into the sterile fluid container 200 (arrows 228). With reference also to FIGS. 6B and 6C, the specialized peristaltic pump 240 may be provided with rotating wheels 244 that have central grooves to receive the coaxial tubing and compress the outer tubing (supply line 210) sufficiently to circulate the sterile fluid 202 therethrough, while not compressing the inner return tubing 225 to an extent which would impede fluid circulation. The outer tubing 210 may be compressed part way to the inner return tubing 225 (as shown), or all the way to the inner return tubing. In the illustrated embodiment, the wheels 244 compress the coaxial tubing against a station set of round surfaces 242 that have corresponding central grooves for receiving the tubing 210.

The respective ends of the supply and return lines 210 and 225 may be spaced apart sufficiently within the container 200 to prevent the air bubbles B being pushed out the return line 225 from re-entering the degassing section 66a through the supply line 210. This may be accomplished in a variety of ways. Foe example, as illustrated in FIG. 6, the ends of the supply and return lines 210 and 225 within the container 200 are longitudinally spaced. Referring to FIG. 6D, in another embodiment, the ends of the supply and return lines 210 and 225 may be coupled to the container 200 in the same manner that supply/return lines 53 and 56 are coupled to the fluid container 50 (FIG. 2) and a "Y" connector 230 may be employed to couple the lines in a coaxial relationship. Here too, the return line 225 and container 200 may be formed from a clear plastic material to allow for visual confirmation that air bubbles B are being removed from the degassing section 66a and pushed through the return line 225 into the container 200.

It will be apparent to those skilled in the art that the inventions may be embodied in other specific forms besides and beyond those described herein. The foregoing embodiments are therefore to be considered in all respects illustrative rather than limiting.

What is claimed is:

1. A system for use with a medical device defining a longitudinal axis, the system comprising:
 a device defining a distal end and a proximal end and including a distal hemostasis valve associated with the distal end, a proximal hemostasis valve associated with the proximal end, an instrument passage lumen located between the hemostasis valves and defining a degassing region with a degassing region distal end and a degassing region proximal end that is longitudinally spaced from and proximal of the degassing region distal end, an inlet port at the degassing region distal end and an outlet port at the degassing region proximal end such that fluid flows only from the degassing region distal end to the degassing region proximal end;
 a source of fluid; and
 a supply line having a first end in fluid communication with the fluid source and a second end in fluid communication with the inlet port.

2. A system as claimed in claim 1, wherein
 the fluid source comprise a container at least partially filled with fluid; and
 the system further comprises a return line having a first end in fluid communication with the outlet port and a second end in fluid communication with the container such that fluid flowing through the outlet port is discharged into the container.

3. A system as claimed in claim 2, wherein the return line is at least partially disposed coaxially within the supply line.

4. A system as claimed in claim 1, further comprising:
 a circulation pump along the supply line.

5. A system as claimed in claim 1, wherein
 the device comprises an introducer sheath including a proximal handle and a guide sheath that defines the instrument passage lumen and degassing region; and
 the inlet and outlet ports are associated with the handle.

6. A system as claimed in claim 1, wherein
 the degassing region distal end abuts the distal hemostasis valve; and
 the degassing region proximal end abuts the proximal hemostasis valve.

7. A system for use with a medical device defining a longitudinal axis, the system comprising:

a device defining a distal end and a proximal end and including
- a proximal hemostasis valve associated with the proximal end,
- a tube extending through the device and defining an instrument passage lumen with a perimeter and a degassing region with a degassing region distal end and a degassing region proximal end that is longitudinally spaced from and proximal of the degassing region distal end, the tube being free of apertures in the degassing region,
- an inlet port at the degassing region distal end that delivers fluid into degassing region from a plurality of locations around the perimeter of the instrument passage lumen, and
- an outlet port at the degassing region proximal end such that fluid flows only from the degassing region distal end to the degassing region proximal end;

a container at least partially filled with a fluid;
a supply line having a first end in fluid communication with the fluid container and a second end in fluid communication with inlet port; and
a return line having a first end in fluid communication with the instrument passage lumen and a second in fluid communication with the fluid container.

8. A system as claimed in claim 7, further comprising:
a circulation pump operatively coupled to the supply line.

9. A system as claimed in claim 7, wherein
the device comprises an introducer sheath including a proximal handle and a guide sheath that defines the instrument passage lumen; and
the inlet and outlet ports are associated with the handle.

10. A system as claimed in claim 7, wherein the return line is at least partially disposed coaxially within the supply line.

11. A system as claimed in claim 7, wherein the inlet port includes an annular lumen that extends around the perimeter of the instrument passage and a plurality of spaced openings that are connected to the annular lumen.

12. A system as claimed in claim 7, further comprising:
a distal hemostasis valve associated with the distal end of the device.

13. A device for use in a vascular access procedure, the device comprising:
- a housing defining a distal end and a proximal end and having an instrument passage lumen extending from the distal end to the proximal end;
- a distal hemostasis valve associated with the distal end of the housing;
- a proximal hemostasis valve associated with the proximal end of the housing;
- an inlet port associated with the housing distal end, proximal of the distal hemostasis valve and in fluid communication with the instrument passage lumen;
- an outlet port proximal of the inlet port and in fluid communication with the instrument passage lumen; and
- at least one brush located within the instrument passage lumen.

14. A device as claimed in claim 13, wherein
the instrument passage lumen defines a longitudinal axis and a perimeter that extends around the longitudinal axis; and
the inlet port delivers fluid from a plurality of locations around the perimeter of the instrument passage lumen.

15. A device as claimed in claim 14, wherein the inlet port includes an annular lumen that extends around the perimeter of the instrument passage lumen and a plurality of spaced openings that are connected to the annular lumen.

16. A device as claimed in claim 15, wherein the inlet port is associated with the distal end of the instrument passage lumen.

17. A device as claimed in claim 13, wherein
the housing comprises a vascular access device handle; and
the instrument passage lumen is defined by a sheath having a portion thereof within the vascular access device handle.

18. A device as claimed in claim 13, wherein the housing is configured to be secured to a vascular access device.

19. A system as claimed in claim 1, wherein the degassing region extends continuously from the distal hemostasis valve to the proximal hemostasis valve.

20. A system as claimed in claim 7, wherein the degassing region distal end and the degassing region proximal end are not equidistant from the inlet port.

* * * * *